United States Patent [19]

Griffin et al.

[11] Patent Number: 5,312,749

[45] Date of Patent: May 17, 1994

[54] INDUSTRIAL ALKALINE PROTEASE FROM SHIPWORM BACTERIUM

[75] Inventors: Harold L. Griffin; Richard V. Grene; Michael A. Cotta, all of Peoria, Ill.

[73] Assignee: The United States of America as represented by the Secretary of Agriculture, Washington, D.C.

[21] Appl. No.: 880,912

[22] Filed: May 12, 1992

[51] Int. Cl.$^5$ .................... C12N 9/52; C12N 9/50; C11D 10/06

[52] U.S. Cl. .................... 435/220; 435/219; 252/174.12

[58] Field of Search .................. 435/219, 220; 252/174.12

[56] References Cited

U.S. PATENT DOCUMENTS

| | | | |
|---|---|---|---|
| 3,723,250 | 3/1973 | Aunstrup et al. | 195/62 |
| 3,840,433 | 10/1974 | Aunstrup et al. | 195/6 |
| 4,749,511 | 6/1988 | Lad et al. | 252/174.12 |
| 4,801,451 | 1/1989 | Hellgren et al. | 424/94.63 |
| 4,861,721 | 8/1989 | Waterbury et al. | 435/252.1 |
| 4,865,983 | 9/1989 | Durham | 435/264 |
| 5,118,623 | 6/1992 | Boguslaski et al. | 435/222 |

FOREIGN PATENT DOCUMENTS

| | | | |
|---|---|---|---|
| 1247025 | 12/1988 | Canada | 195/33.2 |
| 3834550 | 1/1990 | Fed. Rep. of Germany | 435/221 |

OTHER PUBLICATIONS

Imam et al. (1990) *Appl. Environ. Microbiol.*, 56(5), 1317-1322.

Nakano et al. (1979) *Agri. Biol. Chem.*, 43(2), 223-229.

Griffin et al. (1992) *Curr. Microbiol.*, 24(2), 111-117, in *Chem Abst.*, 116(13), 371, Abst. #123, 710.

Harold L. Griffin et al., "Extracellular Endoglucanase Activity by a Novel Bacterium Isolated from Marine Shipworm," Biochemical and Biophysical Research Communication, vol. 144, No. 1, 143-151 (Apr. 14, 1987).

Richard V. Greene et al., "Purification and Characterization of an Extracellular Endoglucanase from the Marine Shipworm Bacterium," Archives of Biochemistry and Biophysics, vol. 267, No. 1, 334-341 (Nov. 15, 1988).

Richard V. Greene et al., "A Novel, Symbiotic Bacterium Isolated from Marine Shipworm Secretes Proteolytic Activity," Current Microbiology, vol. 19, 353-356 (1989).

*Primary Examiner*—Douglas W. Robinson
*Assistant Examiner*—Jon P. Weber
*Attorney, Agent, or Firm*—M. Howard Silverstein; John D. Fado; Curtis P. Ribando

[57] ABSTRACT

A protease has been isolated from a symbiotic bacterium found in the gland of Deshayes of the marine shipworm. The protease remains active over the pH range of about 4–12, exhibits salt tolerance up to 3M sodium chloride, retains a high level of activity above 50° C. for at least 60 min, and is stimulated by oxidizing agents, particularly perborate. The properties of this protease suggest widespread utility in detergents and other low-temperature industrial applications.

4 Claims, 2 Drawing Sheets

INDUSTRIAL ALKALINE PROTEASE FROM SHIPWORM BACTERIUM

BACKGROUND OF THE INVENTION

1. Field of the Invention

This invention relates to a novel protease which has been isolated from a bacterial symbiont of the marine shipworm. The protease is uniquely characterized by stability over a broad pH range as well as tolerance to a variety of chemical environments. These properties render the protease useful in detergents and other low temperature industrial applications.

2. Description of the Prior Art

Proteolytic enzymes are conventionally used in detergent compositions, particularly in laundry detergents. One such enzyme commonly used is subtilisin. This enzyme is produced by Bacillus subtilis and is an effective stain removing agent. Proteolytic enzymes derived from a variety of other Bacillus species have been disclosed by Aunstrup et al. in U.S. Pat. No. 3,723,250. The sources of those species were largely soil samples and manures, and the enzymes were selected for optimal proteolytic activity against hemoglobin at pH above about 9.

Hora (Canadian Patent 1,247,025) recognizes the enzyme stability problems in enzymatic laundry detergents containing peroxide progenitors. Peroxy-type bleaching agents of concern are alkali metal persulphates, perphosphates, perborates, as well as alkali metal and alkaline earth metal salts of organic peracids. Hora discovered that the storage stability of these compositions could be improved by the inclusion of an alkali metal metaborate.

Another factor affecting the stability of proteolytic enzymes is pH. In U.S. Pat. No. 3,840,433, Aunstrup et al. identify a group of proteases produced by the cultivation of Bacillus alcalophilus. These enzymes are useful in the dehairing of hides, and can withstand the highly alkaline pH of a saturated lime solution or of a soda ash solution. Aunstrup et al. contend that the B. alcalophilus proteases exhibit maximum activity against hemoglobin at pH 12 and 25° C. and also at pH 10.1 and 60° C.

Hellgren et al. (U.S. Pat. Nos. 4,801,451 and 4,963,491) teach enzyme preparations from animals of the order Euphausiaceae as being useful in cleaning compositions for degrading and removing contaminants of biological origin. At optimum temperatures of 30°-55° C., these preparations display proteolytic activity in the pH range 5-10.

In U.S. Pat. No. 4,865,983, Durham et al. teach the use of proteases from Vibrio species in cleaning compositions, including laundry detergents, automatic dishwasher detergents, laundry bleaches and presoaks. These proteases are characterized by a high proteolytic activity, stability over wide pH and temperature ranges, and stability to oxidizing agents, including chlorine bleaches.

Lad et al. (U.S. Pat. No. 4,749,511) relate to contact lens cleaning solutions which are comprised of general-purpose proteases in combination with the endoproteinase lys-C for removing lysozyme from lens surfaces. The function of the endopeptidase is to specifically cleave at the carboxyl side of lysine residues and expose susceptible peptide bonds of lysozyme to the protease without concomitant inactivation of the protease. The cleaning solutions of Lad et al. include additional components which aid in the overall lysozyme degradation and solution stability.

In general, enzymes ideal for use in detergents and other cleansing compositions should possess a high level of activity on proteinaceous contaminants over a broad pH range and over a broad temperature range. They should also be stable in the presence of oxidizing agents, bleaches, surfactants and other additives commonly used in detergents. Some detergent applications present less stringent conditions than others and do not require enzymes having the optimum range of tolerances. For example, enzymes for room temperature presoaks and contact lens solutions typically do not require the same temperature stability range as all-temperature laundry detergents. Nonetheless, the search continues to extend the conditions of activity and stability of proteolytic enzymes for all applications.

SUMMARY OF THE INVENTION

We have now discovered a novel protease which remains active over the pH range of about 4-12, exhibits salt tolerance up to saturated NaCl ($>3M$) sodium chloride, retains a high level of activity above 50° C. for at least 60 min, and is stable to cleansing composition constituents, including oxidizing agents and complexing agents. In fact, the novel protease appears to be unique for its characteristic of protease activity stimulation by oxidizing agents, particularly perborate. This enzyme was isolated from a symbiotic bacterium found in the gland of Deshayes of the marine shipworm, Psiloteredo healdi. Its properties suggest widespread utility in cleansing compositions and other low-temperature industrial applications.

In accordance with this discovery, it is an object of the invention to provide a novel proteolytic enzyme in substantially pure form.

It is also an object of the invention to characterize the subject enzyme regarding its useful chemical and physical properties for industrial applications.

It is a further object of the invention to demonstrate the utility of the subject protease in a variety of cleansing compositions, such as laundry detergents and contact lens cleaning solutions.

These and other objects of the invention will become readily apparent from the ensuing description.

DETAILED DESCRIPTION OF THE INVENTION

Figure 1:
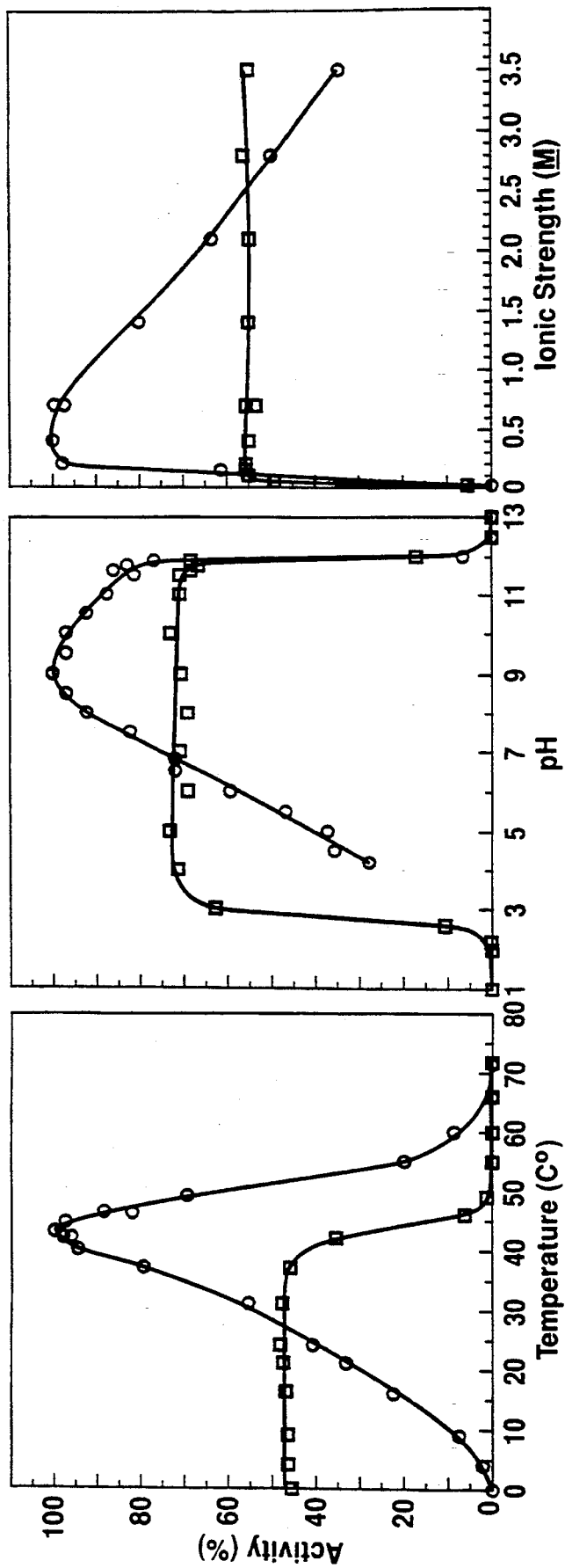
FIGS. 1A, 1B and 1C are plots showing the effects of temperature, pH, and salinity, respectively, on the activity and stability of the purified alkaline protease of the invention.

The source of the protease of the invention is a symbiotic bacterium found as a pure culture in the Gland of Deshayes in many species of wood-boring shipworms which make up a group of bivalve molluscs known as the Teredinidae. As explained by Waterbury et al. in U.S. Pat. No. 4,861,721, herein incorporated by reference, the Gland of Deshayes is unique to the Teredinidae and has historically been associated with the production of cellulolytic enzymes responsible for the wood-boring capability of the mollusc. Bacteria present in this gland were first isolated and reported by Waterbury et al. as being both cellulolytic and nitrogen-fixing. The patent further indicates that bacterial isolates from 15 species within the family Teredinidae were so similar that they likely represent a single species. Also, the fact that the bacterium was successfully isolated from every species of shipworm examined suggests that the bacterium is found in all species of Teredinidae. Accordingly, it is a reasonable expectation that the extracellular protease of the invention can be isolated from the Gland of Deshayes bacterium from all shipworm species. The species of shipworm used as the source of the bacterium for the isolation disclosed herein was *Psiloteredo healdi*. This bacterium is available from the America Type Culture Collection, Rockville, Md., under the Accession Number ATCC 39867.

The shipworm bacterium is readily cultivated on cellulose or other suitable carbon source, preferably, but not necessarily, supplemented with an inorganic nitrogen source. A suitable cultivation temperature would be in the range of 10°–35° C. and preferably 25°–30° C. The optimum cultivation period for a given medium and temperature can be determined by assaying the supernatant activity against a protein substrate, such as azocasein.

In the preferred method of isolating the protease, the whole culture is centrifuged at approximately $10^4$ g to remove cells, and the recovered supernatant is then subjected to ultracentrifugation at approximately $10^5$ g to remove cellular debris. The ultracentrifugation supernatant is concentrated by ultrafiltration and then diafiltered against basal salt ("Amicon PM 30" hollow fiber membrane, Amicon, Danvers, Mass.), and the resulting filtrate is recovered. The diafiltration serves to separate the protease activity from the extracellular endoglucanase activity which is retained in the concentrate [see Greene et al., *Archives of Biochemistry and Biophysics*, vol. 267, 334–341 (1988)]. The combined filtrate from the ultrafiltration and the diafiltrate are further concentrated by ultrafiltration on a "PM 10" hollow fiber membrane (Amicon); and the protease activity is precipitated from the concentrate, such as by bringing the concentrate to 65% saturation with $(NH_4)_2SO_4$. The precipitate is then resuspended and fractionated by gel permeation chromatography. Of course, it is understood that well-known alternatives could be substituted for the various separation steps and that other variations of this scheme would also serve to isolate the proteolytic enzymes.

The apparent molecular mass of the protease of the invention is dependent upon the procedure by which it is determined. Analysis by SDS-PAGE yields a relative molecular mass of 36,000 daltons. When determined by serial gel permeation HPLC, the mass is 17,600±300 daltons. The rate zonal sucrose density-gradient centrifugation method yields a mass of 46,000±2,000 daltons.

While not desiring to be bound by any particular theory, there is a plausible explanation for the large discrepancy in the molecular mass values obtained by the various methods. The low mass (17,600 daltons) obtained by gel permeation HPLC may have resulted from nonspecific interaction of the protein with the column resin, retarding its elution. However, varying the ionic strength of the eluent, addition of detergent or addition of exogenous protein did not significantly alter the elution profile of the protease. A molecular mass of 17,600 is also in good agreement with the nominal molecular weight cutoff values of the ultrafiltration membranes used in the purification scheme described in Example 2. The molecular mass of 36,000 daltons determined by SDS-PAGE and the mass of 46,000 daltons determined by zonal density-gradient centrifugation suggests that the native protease is a dense, tightly folded molecule. For such an enzyme, sedimentation behavior, which is strongly and directly dependent on protein density, would be expected to yield an anomalously high apparent molecular mass relative to standard proteins. Conversely, estimates of molecular mass by HPLC and those suggested by ultrafiltration behavior would be anomalously low, as both determinations depend primarily on the radii of molecules. A denser, more tightly folded molecule should possess a smaller radius in comparison to equivalent molecular mass standards. The molecular mass determined by SDS-PAGE should be close to the actual molecular mass of the protease. Other characteristics of the protease are described in further detail in Example 3.

The activity of the protease of the invention remains unaffected by several compounds known to inhibit various other proteases. For example, sodium perborate, the metal-ion chelators EDTA and Neocuproine HCl, and the cysteine protease inhibitor iodoacetamide have little effect on the enzyme's activity. Phenylmethylsulfonyl fluoride (PMSF), which reacts with the hydroxyl moieties of active site serines in serine proteases, does not inhibit activity. However, tosyl-1-lysine chloromethyl ketone (TLCK), which inhibits serine proteases with trypsin-like activity at the reactive site histidine residue, significantly reduces the activity at low concentrations and abolishes it at high concentrations. In addition, the enzyme is unaffected by tosylamide phenylethyl chloromethyl ketone (TPCK), a chymotrypsin inhibitor, or by $\epsilon$-Amino-n-caproic acid, a plasmin inhibitor.

The high specific activity of the purified protease coupled with its insensitivity to chelating agents and sodium perborate, as well as its stability to an extremely broad range of pH values and ionic strengths renders it useful for a multitude of commercial applications. Without limitation thereto, it is envisioned that the enzyme would be useful in low-temperature laundry detergents, presoaks, household cleaners, body cleansers, contact lens cleaning solutions, dehairing and leather tanning agents, as well as in methods for raw silk cleaning (degumming), silver recovery from photographic film, haze elimination from beers and other beverages, and gelatin manufacturing.

Compositions comprising the protease of the invention may also comprise ingredients and additives conventionally used for the desired application, provided that they do not substantially interfere with the activity of the protease. For example, detergent formulations are likely to include surfactants, soaps, detergents, bleaching agents, builder, soil-suspending agents, pH buffers, buffers, lipases, amylases, cellulases, fragrances, optical brighteners, softening agents, stabilizers, carriers, and the like. Detailed illustrations of such additives are given in Durham et al., supra, herein incorporated by reference. Similarly, dehairing solutions may contain lime, caustic soda, or other alkali such as described in Aunstrup et al., supra, herein incorporated by reference. Hellegren et al., supra, herein incorporated by reference, teach various additives for body cleansers, such as antimicrobials, surfactants, pharmaceutically acceptable carriers, gel formers, etc. As described in Lad et al., supra, herein incorporated by reference, contact lens cleaning solutions may contain various detergents, surfactants, buffers, stabilizers, binders, lubricants, and the like.

Any composition or formulation having as its principal function the cleansing or decontamination of an object, body, or material is defined herein as a "cleansing composition". Cleansing compositions embodying the protease of the invention will typically include one or more nonproteolytic chemical cleansing agent which complements the proteolytic activity in producing the desired cleansing action. Examples of such agents include soaps, detergents, surfactants, and other enzymes.

The enzyme-containing compositions of the invention should contain an appropriate amount of enzyme for achieving the desired end result. For example in laundry detergent compositions, the level of enzyme should be sufficient to degrade at least most of the proteinaceous contaminants likely to be present in soiled clothes. It is understood that the other laundry detergent components discussed above would also play a role in the cleansing action of the composition. Therefore, an effective amount of enzyme would be determined by the nature and amount of other detergent additives in the formulation, as well as by the expected chemical and physical conditions of use. Similar considerations would apply to the selected enzyme level for compositions intended for other applications. In general, the level of proteolytic activity for any given compositions will be in the range of about 10 to 15 enzyme units per milliliter of solution. An enzyme unit is defined as 1 $\mu$g of azoprotein solubilized per hour.

It is also contemplated within the scope of the invention to include the endoglucanase produced by the marine shipworm bacterium as a component of the various compositions described above. This can be accomplished by employing a bacterial culture fraction which comprises both the protease and the endoglucanase, or by recombining these enzymes after separation. As discussed in Griffin et al. [*Biochemical and Biophysical Research Communications*, vol. 144, 143-151 (1987)] and in Greene et al. [*Archives of Biochemistry and Biophysics*, vol. 267, 334-341 (1988)], the endoglucanase produced by the marine shipworm bacterium is useful for initiating cellulose degradation and would therefore be a desirable component in many of the detergent compositions previously discussed.

This invention is further illustrated by the following examples.

EXAMPLE 1

Cell Culture

The bacterial strain (Woods Hole Oceanographic Institution strain number T8301) isolated from *Psiloteredo healdi* shipworm, was a gift of Dr. John Waterbury. Cultures (1 liter) were grown aerobically in 3-liter Fernbach flasks on basal salt medium supplemented with 1% Sigmacell type 50 as a carbon source and 0.10% $NH_4Cl$ as a nitrogen source. The basal medium contained the following, per liter of deionized $H_2O$: $NaCl$, 18.8 g; $KCl$, 0.4 g; $MgSO_4.7H_2O$, 1.9 g; $MgCl_2.6H_2O$, 1.5 g; $CaCl_2.2H_2O$, 0.4 g; HEPES (N-2-hydroxyethylpiperazine-N'-2-ethanesulfonic acid), 4.9 g; solution A, 10 ml; trace metal solution, 1 ml. Solution A consisted of the following (per liter of $H_2O$): $K_2HPO_4.3H_2O$, 2.0 g; $Na_2CO_3$, 1.0 g; sodium citrate, 0.4 g; $Fe_2(SO_4)_3$, 0.3 g; EDTA, 0.05 g. Trace metal solution consisted of the following (per liter of $H_2O$): $H_3BO_3$, 2.9 g; $MnCl_2.4H_2O$, 1.8 g; $ZnSO_4.7H_2O$, 0.2 g; $Na_2MoO_4.2H_2O$, 0.04 g; $CoSO_4.7H_2O$, 0.05 g; $CuSO_4.5H_2O$, 0.08 g. The pH of the basal medium was adjusted to 8.0 with NaOH. The standard growth temperature was 30° C.

EXAMPLE 2

Protease Purification

Cultures (4 × 1 liter) were harvested after 10 days of growth by centrifugation at 15,000 g for 30 min, 4° C. The cell pellet was discarded and the supernatant was ultracentrifuged at 100,000 g at 4° C. for 30 min. The clear, membranous pellet obtained from ultracentrifugation was also discarded. The supernatant was concentrated tenfold by ultrafiltration ("Amicon PM 30" hollow fiber membrane, Amicon, Danvers, Mass.) and then diafiltered with six volumes of distilled water. The combined filtrate and diafiltrate were concentrated to 400 ml by ultrafiltration on an "Amicon PM 10" hollow fiber membrane. The protease activity of the "PM 10" retentate was precipitated by bringing the concentrate to 65% saturation with $(NH_4)_2SO_4$ and collecting the precipitate by centrifugation for 10 min at 10,000 g at 4° C.

The precipitate was resuspended in aqueous 0.1M NaCl containing 20 mM HEPES buffer at pH 7.0. Aliquots of the solution (200 $\mu$l) were applied to a HPLC system fitted in series with a "Bio-sil Sec.250" and a "Bio-sil Sec.125" column (Bio-Rad Laboratories, Richmond, Calif.). The gel permeation system was equilibrated and eluted with aqueous 0.10M NaCl containing 20 mM HEPES buffer at pH 7.0. Fractions containing protease activity were immediately frozen at −72° C. and stored at −20° C. until used.

The protease purification was monitored by assaying for proteolytic activity and protein concentration after each step. Proteolytic activity was determined in duplicate assays employing azocasein for the substrate, as described by Cotta et al. [*Applied Environmental Microbiology*, vol. 52, 51-58 (1986)]. Units represent $\mu$g of azocasein digested per hour. Protein concentrations were determined by the method of Bradford [*Analytical Biochemistry*, vol. 5, 271-283 (1976)] with bovine serum albumin as a standard.

The results of the purification of a protease from 4 liters of cell-free culture medium are summarized in Table I. Ultracentrifugation of cell-free medium removed about half of the protein, while most of the protease activity remained in solution. Further purification was achieved by ultrafiltration as activity passed through a "PM 30" membrane, but was retained by a "PM 10" membrane. This procedure increased the specific activity of the preparation by 1.6-fold, but only after a significant loss in total yield. Much of the loss in yield resulted from activity retention by the "PM 30" membrane. Such activity could not be diafiltered through the "PM 30" membrane. After concentration on the "PM 10" membrane, the protease activity was precipitated with 65% saturated ammonium sulfate and could be sorted indefinitely at −20° C. Gel permeation chromatography allowed purification of the protease to homogeneity as determined by SDS-PAGE. Typically, this purification scheme allowed for a 23-fold increase in specific activity with a 21% yield. It should be noted that these numbers are subject to a certain degree of variability due to competitive inhibition of the azocasein assay by endogenous bacterial protein, as well as autohydrolysis of the enzyme itself.

EXAMPLE 3

Physical Characterization

Solutions of the purified protease from Example 2 at appropriate protein concentrations and in proper solvents for physical characterization were prepared from relatively dilute gel permeation fractions by centrifugal ultrafiltration. This process involved concentrating and washing with appropriate solvents in "Amicon Centricon-10 Microconcentrators" (Amicon 1989 Operating Instructions Centricon Microconcentrators for small volume concentration, publication No. 1-259E).

Molecular Mass

The native molecular mass of the protease was determined by gel permation chromatography and by rate zonal sucrose density-gradient centrifugation; the denatured molecular mass of the protease was determined by sodium dodecyl sulfate-polyacrylamide gel electrophoresis (SDS-PAGE).

The determination by gel permeation chromatography used the HPLC system and mobile phase described above for protease purification. Protein was detected by absorbance at 280 nm and protease activity by the assay previously described. The relative molecular mass of the enzyme was interpolated from a plot of log molecular mass versus retention time for standard proteins. The average mass value of five determinations by this method was $17,600 \pm 300$ daltons.

For rate zonal sucrose density-gradient centrifugation, aliquots (0.1 ml) of purified protease and marker protein solutions were layered on 4.0 ml of a 5-20% linear sucrose gradient in 4.4 ml polyallomer centrifuge tubes. All solutions were buffered at pH 7.0 with 20 mM HEPES buffer containing 0.1M NaCl. The tubes were centrifuged 17.5 hr at 50,000 rpm in a swinging bucket rotor (SW 56 Ti, Beckman Instruments, Inc., Palo Alto, Calif.) at 2° C. After centrifugation, the contents of the tubes were analyzed for absorbance at 254 nm and fractionated using an "Isco Density Gradient Fractionator". The fractions (0.25 ml) were assayed for protease activity. Distance sedimented by the marker proteins [Ribonuclease A (13,700) chymotrypsinogen A (25,000), ovalbumin (45,000), Aldolase (158,000)] was calculated from the position of maximum absorption at 254 nm. Distance sedimented by the protease was calculated from the position of maximum protease activity. The relative molecular mass of the protease was interpolated from a plot of log molecular mass versus log distance sedimented for the marker proteins. The average value for three determinations was $46,000 \pm 2000$.

Determination of denatured molecular mass by SDS-PAGE was performed by the method of Laemmli [*Nature*, vol. 227, 680–685 (1970)] using a "PhastSystem" (Pharmacia, Piscataway, N.J.) and a precast continuous 10–15% polyacrylamide gradient gel with 2% cross-linking. Bands were detected by silver staining. The relative molecular mass of the protease was interpolated from a plot of log molecular mass versus relative mobility for standard proteins. A single band with a relative molecular mass of 36,000 daltons was obtained.

Isoelectric Point

Nondenaturing isoelectric focusing was also performed with the "PhastSystem" using "PhastGel IEF 5-8", a homogenous polyacrylamide gel containing "Pharmalyte" carrier ampholytes that generate a linear pH gradient from pH 5.85 to pH 10.25 during electrophoresis. Bands were detected by silver staining. The pI of the protease was interpolated from a plot of pI for standard proteins versus their distance from the cathode after reaching equilibrium position. This method revealed an alkaline doublet at pH 8.53 and pH 8.63 indicating protein microheterogeneity.

Proteolytic Activity

Proteolytic activity was detected by blotting identically run but unstained IEF "PhastGels" onto a Bio-Rad agar diffusion plate (10 mm thick 1% agar gel containing bovine casein in Tris-buffered saline, pH 7.4), for 16 hr at ambient temperature. Following removal of the "PhastGel", the casein agar was layered with 5% acetic acid in 10% aqueous ethanol to precipitate undigested bovine casein. A clearing zone, indicative of proteolytic activity, became readily apparent and was centered around the doublet.

Carbohydrate Content

Carbohydrate content of the protease was determined by the phenol-sulfuric acid method of Dubois et al. [*Analytical Chemistry*, vol. 28, 350–356 (1956)]. Sufficient frozen active gel permeation fractions to contain $>100$ μg of protease protein were concentrated with "Amicon Centricon-10" microconcentrators to 0.5 ml and were washed with six volumes of distilled water to remove free sugars. The sample was then assayed for carbohydrate using glucose as the standard. Within the detection limits of the phenol-sulfuric acid assay (1%), no carbohydrate appeared to be associated with the enzyme.

Temperature, pH, Salinity Dependence, and Stability

As shown in FIGS. 1A, 1B and 1C, the effects of temperature, pH, and salinity respectively, on the activity of the purified protease were determined. The stability (□) of the protease against each factor was determined by preincubation at the indicated temperatures, pHs, and salinities for 60 min and then reacting with azocasein in standard assays. The standard azoprotein assay was reacted 3 hr at 25° C., pH 6.8, and 0.10M NaCl. The activity dependence (o) of the protease on each factor was determined by adjusting the standard azocasein assay to the temperature, pH, or salinity indicated. Maximum relative activity corresponds to 150 units/ml.

Maximum activity was observed at 42° C., pH 9.0, and 0.20M NaCl. The enzyme was unstable at temperatures exceeding 40° C., below 0.10M NaCl, and at pH values below 3.0 or above 11.9. Activity reduction above 0.40M NaCl could have related to physical changes in the assay substrate. That is, visible precipitation of the azocasein occurred at high salinities. The loss of protease activity noted at NaCl below 0.10M was accompanied by significant aggregation. In water, the $M_r$ of the major protein is near 168,000 daltons (gel permeation HPLC analysis) and only about 6% of the original activity remained. Such aggregation could be prevented and nearly half of the protease activity retained by including a substrate (0.02% BSA) in the solvent. Loss of activity that occurred above 42° C. (FIG. 1A) was not stabilized significantly by added salt or substrate.

The purified enzyme had a specific activity of 11,240 proteolytic units/mg measured in the standard assay (25° C., pH 6.8, and 0.10M Nacl). At optimum conditions (42° C., pH 9.0, and 0.20M NaCl), this value was increased to 65,840 units/mg. The enzyme was stable under these conditions for at least 12 hr. However, under conditions of instability (temperatures greater than 42° C., salinities below 0.10M, and pH above 11.9 and below 3.0), the activity half-life was less than 30 min.

EXAMPLE 4

Inhibition of Protease Activity

Several compounds known to inhibit various proteases were examined for their effect on the activity of the purified enzyme from Example 2 (Table II). The protease was incubated prior to assay for 1 hr at 25° C. (except where noted) in buffer containing the inhibitor at the concentrations shown in the Table. All assays were measured at 42° C. and pH 9.0 in 0.2M NaCl buffered with 100 mM bis Tris propane. One hundred percent activity with no inhibitor present was 154 units/ml.

Of particular significance from the data presented in Table II is the apparent enhancement of protease activity produced by the sodium perborate tetrahydrate over a range of temperatures. The effect of oxidants on protease activity was further investigated in Example 5, below.

EXAMPLE 5

Effect of Oxidants on Protease Activity

Figure 2:
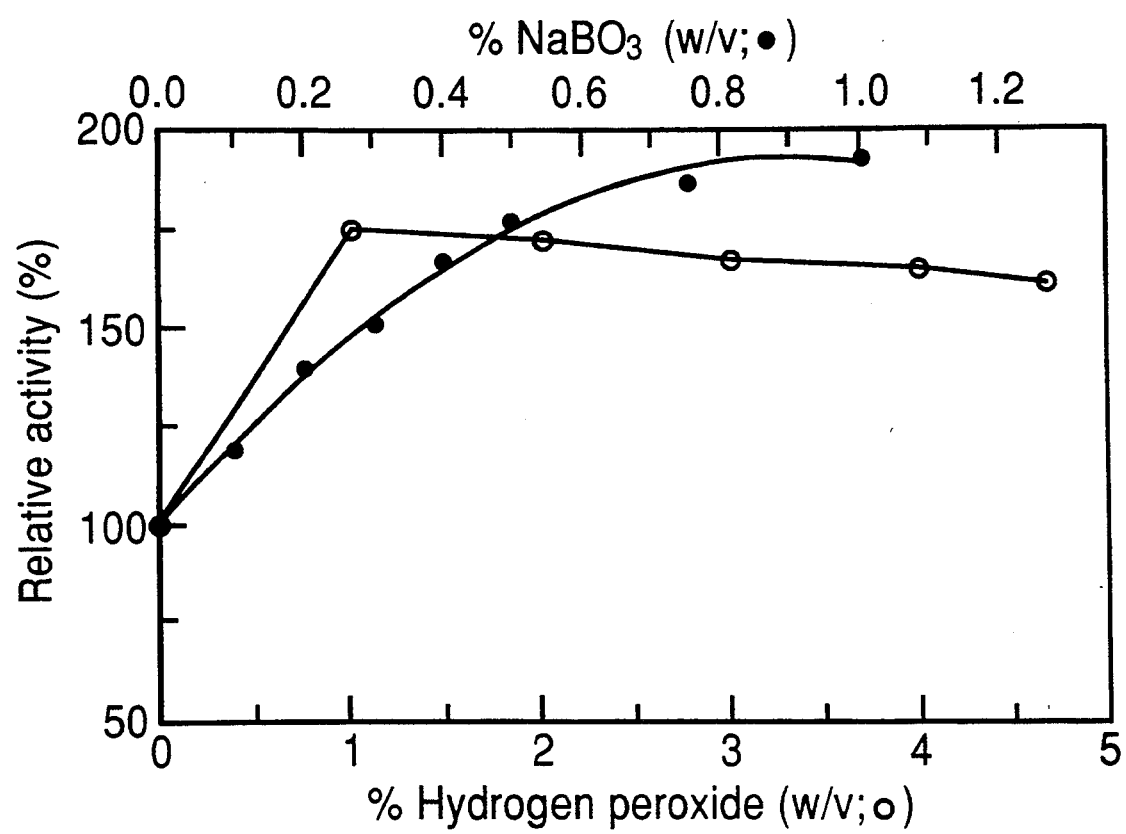
FIG. 2 is a pair of plots showing the effects of $NaBO_3$ and $H_2O_2$ on the relative activity of the purified protease of the invention.

The effects of hydrogen peroxide and sodium borate on the activity of the alkaline protease were investigated. Samples containing 224 units of protease were incubated in the presence of the oxidant for 3 hr at 25° C. Bis Tris propane (20 mM) in 0.15M NaCl was used to buffer the system at pH 9.0. The relative activity on azocasein is plotted versus the weight percent of hydrogen peroxide (○) or $NaBO_3$ (·) in FIG. 2.

EXAMPLE 6

Amino Acid Analysis and Sequencing

Sequencing and amino acid composition of the protease was performed by automated Edman degradation on an Applied Biosystems (San Jose, Calif.) 477A pulsed-liquid phase sequencer by Dr. Saw Kyin (University of Illinois Biotechnology Center).

Table III presents the amino acid composition of the purified protease based on a relative molecular weight of 36,000 daltons. As suggested by the high isoelectric point, the enzyme was rather rich in basic residues. The basic residues, histidine, arginine, and lysine, represented 10% of the protein hydrolysate. The sequence obtained for the first 10 residues of the enzyme was Ile-val-tyr-pro-arg-val/ala-gly-met-ser (SEQ ID NO 1). Within the error limits of the assay, residue number 6 was uncertain and assigned either valine or tyrosine with valine being more probable.

EXAMPLE 7

Effect of Protease Presoaking on Cleansing Power of Detergent

Washing experiments were carried out using swatches of EMPA 116 test cloth uniformly soiled with blood, milk, and carbon black.

The detergent used in these experiments was AATCC Standard detergent 124 without brightener having the following composition:

| | |
|---|---|
| Linear alkysulfonate-sodium salt (LAS) | 14.00% |
| Alcohol ethoxylate | 2.30% |
| Soap-high molecular mass | 2.50% |
| Sodium triplyphosphate | 48.00% |
| Carbonate | 0.00% |
| Alumino silicate solids | 0.00% |
| Sodium silicate ($SiO_2/Na_2O$ = 2.0:1 ratio) | 9.70% |
| Sodium sulfate | 15.40% |
| Carboxymethylcellulose (CMC) | 0.25% |
| Sodium polyacrylate | 0.00% |
| Moisture and miscellaneous | 7.85% |
| Brightener 15 | 0.00% |

Other conditions were as follows:

| | |
|---|---|
| Water hardness | 5 ppm |
| Fabric to water ratio | 1:40 |
| Wash time | 30 min |
| pH | 9.0 |
| Detergent concentration | 0.40% (wt basis) |

For this example, the protease was used as a presoak in the following process. At zero time, 10 ml of enzyme solution at pH 9.0 containing 1200 units of azocasein activity was pipetted into a 150-ml beaker containing 90 ml of tap water or sea water which was equilibrated and thermostatted at 50° C. Concurrently, 2.5 g of the test fabric was added to the contents of the beaker and allowed to soak for 30 min. Controls were run using tap water and sea water presoaks without protease as well as elimination of the presoak step altogether. At the end of the presoak period, the fabric was lifted out of the beaker and placed into another 150-ml beaker containing 90 ml of wash solution (tap water with detergent) which was equilibrated and thermostatted at 50° C. Every 4 min the contents of the beaker were agitated for 10 sec with a glass rod. After 30 min the wash solution was drained, and the test swatches were rinsed in running tap water for 10 min. They were subsequently air-dried and ironed. The remission of the ironed swatches was measured in a LI-COR Portable Spectraradiometer equipped with an integrating sphere at 480 nm. Remission values were standardized against $BaSO_4$. The reported remissions indicate average values from six randomly selected swatch locations. The results are reported in Table IV.

EXAMPLE 8

The procedure of Example 7 was repeated except that the enzyme solution was combined with the wash solution prepared from either tap water or sea water, and the presoak step was eliminated. Controls included tap water and sea water detergent solutions without protease or with autoclaved protease. The results are reported in Table V.

EXAMPLE 9

The procedure of Example 8 was repeated using tap water plus enzyme as the wash solution at four different temperatures. The results are reported in Table VI.

It is understood that the foregoing detailed description is given merely by way of illustration and that modification and variations may be made therein without departing from the spirit and scope of the invention.

TABLE I

Summary of Purification of Alkaline Protease from Shipworm Bacterium

| Fraction | Total protein (mg) | Total activity (U · 10³)* | Specific activity [(U/mg) · 10³]* | Fold purification | Yield (%) |
|---|---|---|---|---|---|
| Whole culture | ... | 384.0 | ... | ... | ... |
| Centrifuge supernatant | 760 | 369.5 | 0.49 | 1.0 | 100 |
| Ultracentrifuge supernatant | 344 | 277.8 | 0.81 | 1.6 | 75 |
| "PM 10" retentate | 34 | 47.2 | 1.39 | 2.8 | 13 |
| (NH$_4$)$_2$SO$_4$ precipitate | 28 | 39.6 | 1.41 | 2.9 | 11 |
| Gel permeation HPLC | 7 | 78.7 | 11.24 | 22.9 | 21 |

*Units (U) are micrograms of azoprotein solubilized per hour.

Table II

Inhibition of Alkaline Protease

| Inhibitor (class) | Inhibitor | Conc. of inhibitor | Activity (%) |
|---|---|---|---|
| Serine and cysteine protease inhibitor | Phenylmethanesulphonyl fluoride | 0.1 mM<br>1 mM<br>10 mM | 93<br>98<br>102 |
| Trypsin, plasmin, thrombin, and cysteine protease inhibitors | TLCK | 0.1 mM<br>1 mM<br>10 mM | 47<br>20<br>7 |
| Chymotrypsin and cysteine protease inhibitor | TPCK | 0.1 mM<br>1 mM<br>10 mM | 94<br>99<br>100 |
| Plasmin and trypsin protease inhibitor | ε-Amino-n-caproic acid | 100 μg<br>500 μg | 101<br>99 |
| Cysteine protease inhibitor | Iodoacetamide | 0.1 mM<br>1 mM<br>10 mM | 102<br>102<br>100 |
| Heavy-metal ions | CuCl$_2$ | 0.1 mM<br>10 mM | 97<br>94 |
|  | HgCl$_2$ | 0.1 mM<br>10 mM | 66<br>8 |
| Metal-ion chelators | EDTA (disodium salt)<br>Neocuproine HCl | 10 mM<br>10 mM | 102<br>99 |
| Bleaching agent | Sodium perborate tetrahydrate | 0.1%<br>(25° C.)<br>(42° C.) | 119<br>117 |

TABLE III

Amino Acid Composition of Alkaline Protease

| Amino acid | Molecular ratios Average | Nearest integer |
|---|---|---|
| Aspartic acid/asparagine | 40.59 | 41 |
| Glutamic acid/glutamine | 2.07 | 2 |
| Serine | 25.29 | 25 |
| Glycine | 32.77 | 33 |
| Histidine | 5.20 | 5 |
| Arginine | 17.26 | 17 |
| Threonine | 16.91 | 17 |
| Alanine | 34.07 | 34 |
| Proline | 10.91 | 11 |
| Tyrosine | 16.37 | 16 |
| Valine | 34.22 | 34 |
| Methionine | 1.00 | 1 |
| Isoleucine | 21.92 | 22 |
| Leucine | 17.41 | 17 |
| Phenylalanine | 9.32 | 9 |
| Lysine | 6.52 | 6 |

TABLE IV

Effect of Protease Presoaking on Cleansing Power of Detergent

Remission of EMPA-test swatch No. 116

| Presoak solution | Untreated | After presoaking and rinsing | After washing presoaked swatch in tap water with detergent |
|---|---|---|---|
| None | 10.1 | ... | 20.3 |
| Tap water | ... | 15.4 | 34.1 |
| Tap water + protease | ... | 21.9 | 45.4 |
| Sea water | ... | 12.5 | 36.0 |
| Sea water + protease | ... | 11.2 | 43.0 |

TABLE V

Effect of Protease Addition on Cleansing Power of Detergent

| Detergent wash solution | Remission of EMPA-test swatch No. 116 After washing |
|---|---|
| Tap water | 20.3 |
| Tap water + protease | 34.7 |
| Tap water + autoclaved protease | 21.7 |
| Sea water | 14.7 |
| Sea water + protease | 16.0 |
| Sea water + autoclaved protease | 14.4 |

TABLE VI

Effect of Temperature on Cleansing Power of Detergent with Protease Additive

| Detergent wash solution | Remission of EMPA-test Swatch No. 116 | | | |
|---|---|---|---|---|
|  | 25° | 30° | 40° | 50° |
| Tap water | ... | ... | ... | 21.7 |
| Tap water + enzyme | 37.4 | 35.0 | 35.7 | 37.7 |

EXAMPLE 6

Printing plates manufactured by using a Xenon lamp are described in this example.

Lithographic plates were obtained by the same method as described in Example 1, except that diethylene glycol dimethacrylate was used for the photopolymerizable compound, the compound illustrated below was used for the photopolymerization initiator, the ink absorbing layer composition 2 in Example 4 was used for the ink absorbing layer composition and the surface of the ink absorbing layer bearing image parts was exposed to a light beam of a Xenon lamp (output 150W). An evaluation of the image quality of the lithographic plate gave a good result without any spread.

We claim:

1. A substantially pure protease isolated from a culture of bacterium found in the gland of Deshayes of the marine shipworm in the family Teredinidae, said protease having a molecular mass of about 36,000 daltons as determined by SDS-PAGE, having a isoelectric point of about pH 8.6, and having the property that the proteolytic activity thereof is stimulated by perborate or peroxide.

2. A protease as described in claim 1 wherein said marine shipworm is *Psiloteredo healdi*.

3. A protease as described in claim 2 wherein said bacterium has all the identifying characteristics of the deposited culture ATCC 39867.

4. A proteolytic composition consisting essentially of the protease described in claim 1 and a carrier for said protease.

* * * * *

SEQUENCE LISTING (1) GENERAL INFORMATION:

SEQUENCE LISTING (i) APPLICANT: Griffin, Harold L.
    Greene, Richard V.
    Cotta, Michael A.
(ii) TITLE OF INVENTION: Industrial Alkaline Protease From Shipworm Bacterium
(iii) NUMBER OF SEQUENCES: 1
(iv) CORRESPONDENCE ADDRESS:
  (A) ADDRESSEE: Curtis P. Ribando
  (B) STREET: 1815 North University Street
  (C) CITY: Peoria
  (D) STATE: IL
  (E) COUNTRY: USA
  (F) ZIP: 61604
(v) COMPUTER READABLE FORM:
  (A) MEDIUM TYPE: Floppy disk
  (B) COMPUTER: IBM PC compatible
  (C) OPERATING SYSTEM: PC-DOS/MS-DOS
  (D) SOFTWARE: PatentIn Release #1.0, Version #1.25
(vi) CURRENT APPLICATION DATA:
  (A) APPLICATION NUMBER:
  (B) FILING DATE:
  (C) CLASSIFICATION:
(viii) ATTORNEY/AGENT INFORMATION:
  (A) NAME: Ribando, Curtis P
  (B) REGISTRATION NUMBER: 27976
(ix) TELECOMMUNICATION INFORMATION:
  (A) TELEPHONE: 309-685-4011 ext. 513
  (B) TELEFAX: 309-685-4128
(2) INFORMATION FOR SEQ ID NO:1:
  (i) SEQUENCE CHARACTERISTICS:
    (A) LENGTH: 10 amino acids
    (B) TYPE: amino acid
    (D) TOPOLOGY: linear
  (ii) MOLECULE TYPE: protein
  (vi) ORIGINAL SOURCE:
    (A) ORGANISM: Psiloteredo healdi
    (C) INDIVIDUAL ISOLATE: ATCC 39867
  (ix) FEATURE:
    (A) NAME/KEY: Region
    (B) LOCATION: 1 . . . 10
    (D) OTHER INFORMATION: /note = "This sequence represents the first 10 residues of the protease isolated in Example 2"
  (xi) SEQUENCE DESCRIPTION: SEQ ID NO:1:

Ile Val Tyr Pro Arg Val Ala Gly Met Ser
1               5                    10